United States Patent [19]

St. Germain et al.

[11] Patent Number: 5,534,007
[45] Date of Patent: Jul. 9, 1996

[54] STENT DEPLOYMENT CATHETER WITH COLLAPSIBLE SHEATH

[75] Inventors: Jon P. St. Germain, Elk River; Scott A. Olson, Zimmerman, both of Minn.

[73] Assignee: SciMed Life Systems, Inc., Maple Grove, Minn.

[21] Appl. No.: 444,822

[22] Filed: May 18, 1995

[51] Int. Cl.$^6$ .................................................. A61B 17/00
[52] U.S. Cl. ......................... 606/108; 606/191; 606/198
[58] Field of Search ..................................... 606/108, 191, 606/198, 194, 195, 200; 623/1, 12

[56] References Cited

U.S. PATENT DOCUMENTS

| | | | |
|---|---|---|---|
| 4,787,899 | 11/1988 | Lazarus | 623/1 |
| 5,026,377 | 6/1991 | Burton et al. | 606/108 |
| 5,151,105 | 9/1992 | Kwan-Gett | 623/1 |
| 5,188,635 | 2/1993 | Radtke | 606/198 X |
| 5,250,070 | 10/1993 | Parodi | 606/194 |
| 5,263,963 | 11/1993 | Garrison et al. | 606/198 |
| 5,389,100 | 2/1995 | Bacich et al. | 606/108 |
| 5,411,507 | 5/1995 | Heckele | 606/108 |
| 5,456,667 | 10/1995 | Ham et al. | 606/198 X |

FOREIGN PATENT DOCUMENTS 3001849  2/1993  WIPO ................................... 606/198

*Primary Examiner*—Michael H. Thaler
*Assistant Examiner*—Patrick W. Rasche
*Attorney, Agent, or Firm*—Vidas, Arrett & Steinkraus

[57] ABSTRACT

The present invention provides an improved stent delivery catheter. The stent delivery system comprises a catheter having a stent receiving portion adapted to receive a stent near the distal end of the catheter and a stent concentrically arranged around the catheter within the stent receiving portion. The stent delivery system further comprises a proximal outer sheath, a retractable distal sheath surrounding at least a portion of the stent and containing the stent in its reduced delivery configuration and a pull back means connected to the retractable distal sheath. The system further comprises a collapsible sheath concentrically arranged around the catheter and located between the retractable distal sheath and the proximal outer sheath, whereby when the pull back means is pulled proximally the distal sheath is retracted, causing the collapsible sheath to collapse and freeing the stent for delivery.

40 Claims, 3 Drawing Sheets

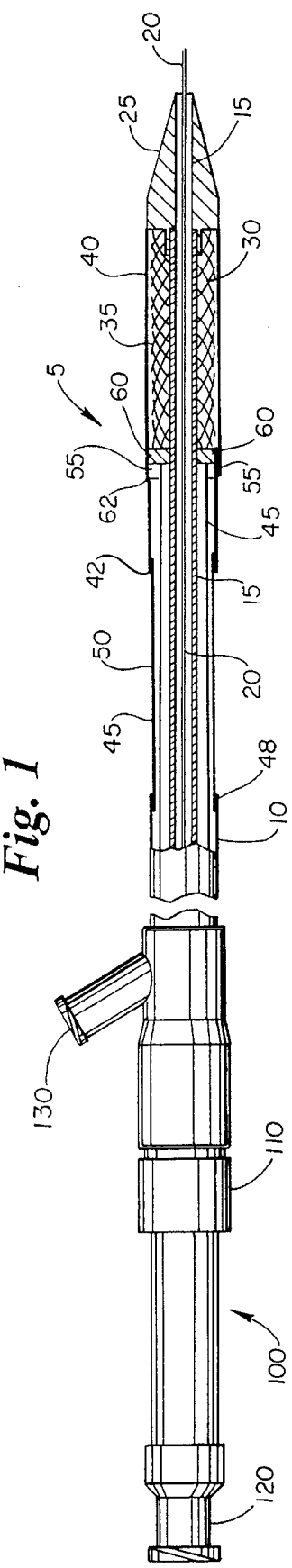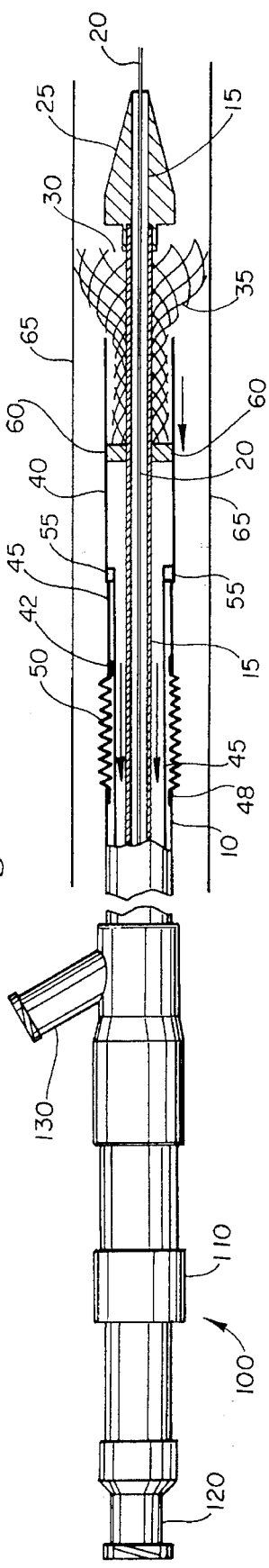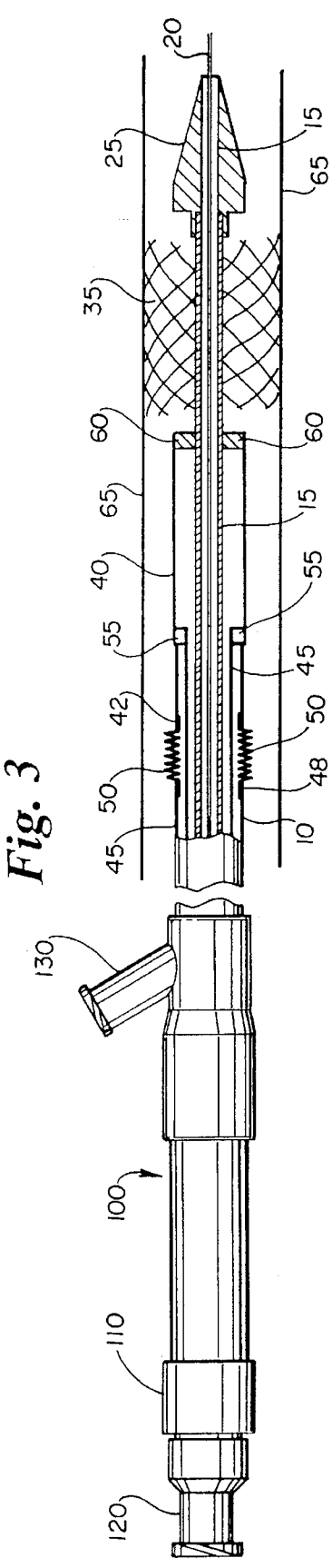

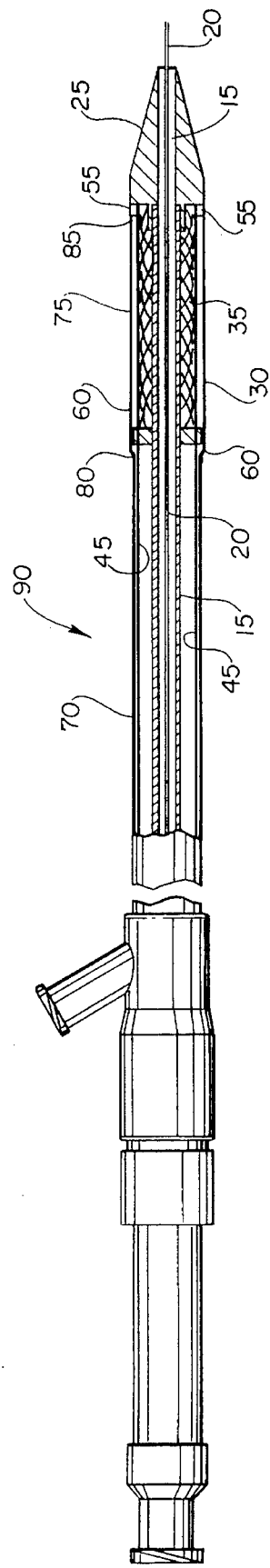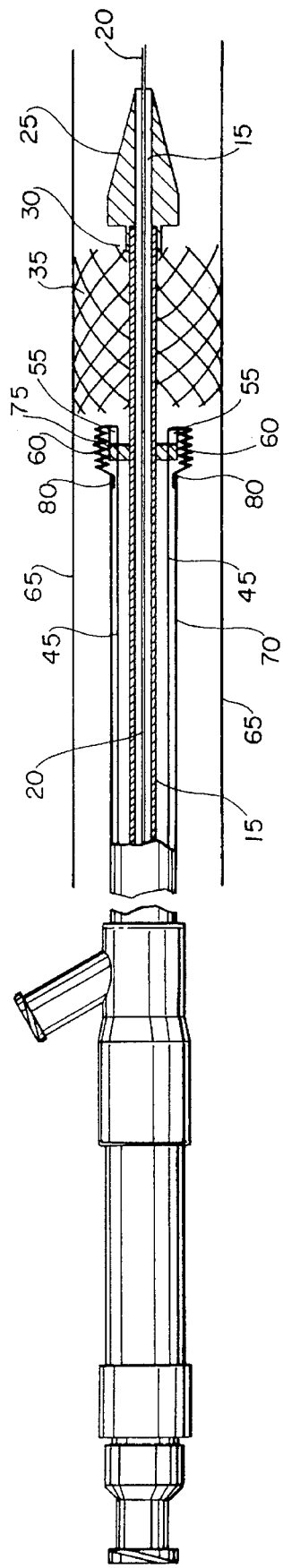

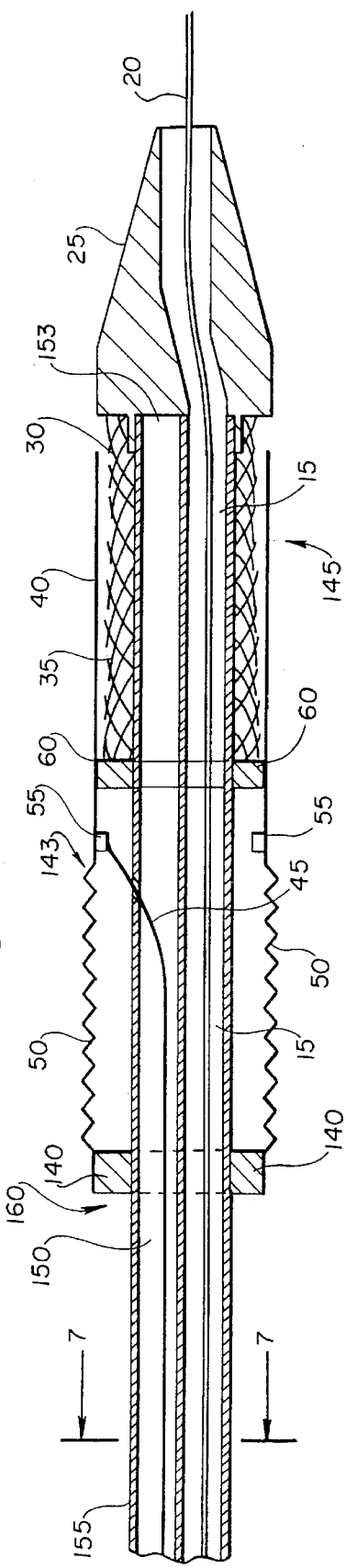
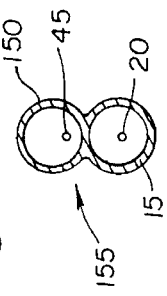
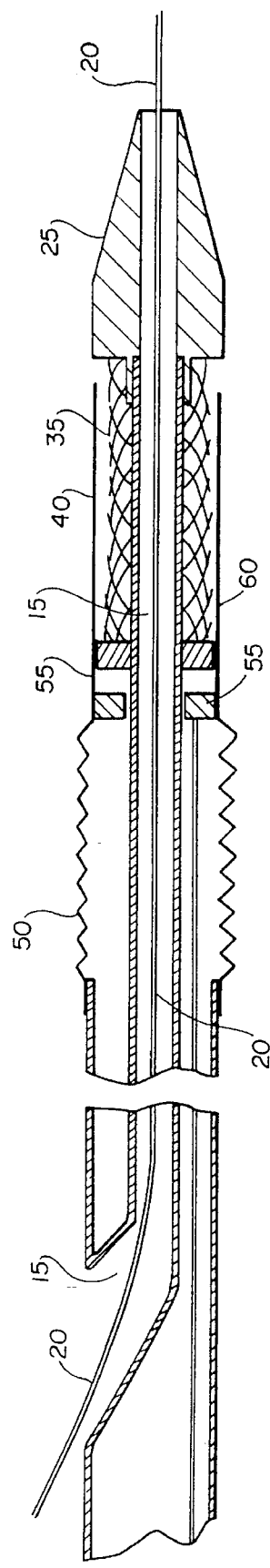

STENT DEPLOYMENT CATHETER WITH COLLAPSIBLE SHEATH

FIELD OF THE INVENTION

This invention relates to a stent delivery catheter system, such as the kind used in percutaneous transluminal coronary angioplasty (PTCA) procedures. More particularly, it relates to a stent delivery catheter employing a collapsible sheath which collapses during the retraction of a distal sheath during the release of a self-expanding or balloon expandable stent.

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon catheter could be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside the artery at the lesion. The stent may either be a self-expanding stent or a balloon expandable stent. For the latter type, the stent is often delivered on a balloon and the balloon is used to the expand the stent. The self-expanding stents may be made of shape memory materials such as nitinol or constructed of regular metals but of a design which exhibits self expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is retracted to expose the stent. After the sheath is removed, the stent is free to self-expand or be expanded with a balloon.

In a coronary stent deployment system which utilizes a retractable sheath one problem which is encountered is the interaction of the sheath and guide catheter upon retraction. The traditional way of dealing with this is to make the retractable sheath long enough so that it will be contained in the guide catheter at all times. This increases system profile, reduces flexibility and creates excess friction upon sheath retraction. The invention disclosed reduces the sheath length, maintains a reduced system profile and provides good flexibility.

SUMMARY OF THE INVENTION

The present invention provides an improved stent delivery system. The stent delivery system comprises a catheter having a proximal outer, a stent receiving portion adapted to receive a stent near the distal end of the catheter, a retractable distal sheath concentrically arranged around the stent receiving portion and a pull back means connected to the distal sheath. The catheter further comprises a collapsible sheath located between and adhered to the proximal outer sheath and the retractable distal sheath. During retraction of the distal sheath the collapsible sheath collapses upon itself, or accordions upon its preformed pleats or creases, providing room for the distal sheath to retract unencumbered, thereby freeing the loaded stent. The inclusion of the collapsible sheath significantly reduces the sheath length, maintains a reduced system profile, provides good flexibility and provides a protective covering to the wire pull back mechanism.

Other objects, features, embodiments and characteristics of the present invention, as well as the methods of operation and functions of the related elements of the structure, and the combination of parts and economics of manufacture, will become more apparent upon consideration of the following description with reference to the accompanying drawings, all of which form a part of this specification.

BRIEF DESCRIPTION OF THE FIGURES

FIG. 1 shows a side view of a catheter according to the invention having a loaded stent including a cross-sectional view of the distal portion thereof and a side view of the proximal end of a catheter according to the invention showing the manifold portion thereof.

FIG. 2 shows a side view of a catheter according to the invention having a loaded stent including a cross-sectional view of the distal portion thereof, wherein the loaded stent is shown as partially deployed, and a side view of the proximal end of a catheter according to the invention showing the manifold portion thereof.

FIG. 3 shows a side view of a catheter according to the invention having a loaded stent including a cross-sectional view of the distal portion thereof, wherein the loaded stent is shown as fully deployed and a side view of the proximal end of a catheter according to the invention showing the manifold portion thereof.

FIG. 4 shows a side view of a catheter according to an alternative embodiment of the invention having a loaded stent including a cross-sectional view of the distal portion thereof.

FIG. 5 shows a side view of a catheter according to an alternative embodiment of the invention having a loaded stent including a cross-sectional view of the distal portion thereof, wherein the loaded stent is shown as fully deployed.

FIG. 6 shows a side view of a catheter according to an alternative embodiment of the invention having a loaded stent including a cross-sectional view of the distal portion thereof.

FIG. 7 is a sectional view of the catheter thereof, taken along line 7—7 in FIG. 6.

FIG. 8 shows a side view of a catheter according to an alternative embodiment of the invention having a loaded stent including a cross-sectional view of the distal portion thereof.

DETAILED DESCRIPTION OF THE INVENTION

FIG. 1 shows a cross-section of the distal portion of a specific embodiment of the stent delivery catheter, generally designated as 5, that is the subject of the present invention. The device generally comprises a proximal outer 10 which covers the majority of the catheter 5 excluding a portion of the distal end of the catheter 5. This outer 10 is characterized by a flexible tube which contains a pull wire lumen and a guide wire lumen. Preferably the outer 10 is comprised of a high density polyethylene (HDPE) or SURLYN material. The proximal outer 10 encloses an optional guide wire lumen 15 which extends through and terminates with the distal tip 25 of the catheter 5. Preferably the guide wire lumen 15 encloses a guide wire 20 which aids in the navigation of the catheter 5 through the appropriate vessel. The guide wire lumen 15 is made of flexible, but incompressible construction such as a polymer encapsulated braid or coil. The flexibility of the braid/coil allows the catheter 5 to navigate through body lumens and the incompressibility of the braid/coil aids in maintaining the integrity of the catheter and aids in deployment accuracy when the sheath is being retracted during stent release. The braid/coil may be comprised of stainless steel or nitinol, but preferably stainless steel encased in a polymer such as a polyimide, HDPE, teflon or urethane, but preferably polyimide or teflon.

Situated just proximal to the distal tip 25 is the portion 30 of catheter 5 around which the stent is concentrically carried. The stent 35 surrounds the guide wire lumen 25. The stent 35 is preferably a Nitinol™ or mesh self-expanding stent, but may also be a balloon expandable stent carried by an expansion balloon. Self-expanding and balloon expandable stents are well known in the art and require no further instruction.

The present invention further comprises a retractable distal sheath 40 which covers and contains the loaded stent 35. The retractable distal sheath 40 will hold a self-expanding stent in its reduced delivery configuration. The retractable distal sheath will merely contain a balloon expandable stent which was positioned over an expansion balloon. The distal sheath 40 is connected to a retracting member 45, or pull wire, which allows a physician to retract the distal sheath 40 from the proximal end of the catheter 5, thus releasing the stent 35 in the targeted area of the vessel. The retractable sheath 40 may be flexible or rigid, and is generally used to retain the stent 35 and protect the vessel wall. The distal sheath is preferably formed of a material which provides tensile strength, but is flexible, such as a braid, coil, a super elastic alloy, polymer, stainless steel or other similar composites. The retracting member 45 may be a rod, a cable, a tube which may also be used to transport fluids, a pull back wire, guide wire or the like, but is preferably a wire. In addition, the retracting member 45 may be tapered along its length to impart varying flexibility. Those skilled in the art will recognize other suitable materials and constructions may be employed to serve substantially the same function. The figures show two pull wires, but one is preferred. It should be understood that any desired number of pull wires could be utilized. The retracting member 45 extends longitudinally within the proximal outer 10, optionally through a retracting member lumen (not shown), such as a HDPE, nylon, or polyether block amide (PEBAX) tube. In one embodiment, the retracting member lumen extends longitudinally under the proximal outer 10, and houses the pull back wire 45. The retracting member lumen that houses the pull back wire 45 may also carry fluid for purging air from the catheter 5.

The invention additionally comprises a collapsible sheath 50 situated between the proximal outer 10 and the distal sheath 40. The collapsible sheath 50 covers the exposed area between the proximal outer 10 and the distal sheath 40, serving to protect the guide wire lumen 15 and the retracting member 45 in this area. The collapsible sheath 50 is adhered to the proximal end of the distal sheath 40 at point 42 and the distal end of the proximal outer 10 at point 48. These connections between components are preferably made using adhesives such as urethane or cyanoacrylate, and other suitable adhesives that are well known in the art. Connections between polymer components can also be made using other bonding techniques such as thermal welding, ultrasonic welding and the like.

The collapsible sheath 50 is manufactured to induce collapsibility by winding a coil around the collapsible sheath material, such as a tube of SURLYN. The coil winder controls the pitch or distance between adjacent wraps of wire. After the tube is wound, the tube is pressurized, causing the material to expand between the gaps in the wire and creating the pleats or creases which allow it to collapse. The coil is then removed producing the collapsible sheath 50 behind.

As the distal sheath 40 is retracted, the collapsible sheath 50 is forced back, collapsing upon itself into an accordion type configuration to give the distal sheath 40 room to retract. The collapsible sheath 50 is longer than the distal sheath 40 and is made from a highly flexible material such as SURLYN, PEBAX, or LDPE, but preferably SURLYN. The distal sheath 40 and the collapsible sheath 50 may be two separate sheaths adhered to one another, or they may form one continuous sheath.

In the preferred embodiment, the distal sheath 40 is connected via a collar comprised of a short section of hypotube 55, configured as an annular ring, to the pull back wire 45. The proximal end of the distal sheath 40 is attached by adhesive or heat bond to the annular ring 55 and the distal end of the pull back wire 45 is connected, preferably brazed, to the inside of the annular ring 55. Although one pull back wire 45 is preferred, a plurality of pull back wires may be connected to the collar 55. The illustrative figures enclosed herein utilize one pull back wire.

Proximal to the stent 35 is a stopper 60. The stopper 60 is preferably HDPE and is attached to the guide wire lumen 15, or whatever may comprise the rigid inner core, and is used to prevent the stent 35 from moving proximally when the distal sheath 40 is retracted.

Preferably, the catheter 5 further comprises an optional neck portion 62 located just proximal to the collar 55. This portion 62 is a slight reduction in diameter of the catheter 5 just behind the collar 55. The neck portion 62 aids in containing the collar 55 and supplies added leverage to the collar 55 as it retracts the distal sheath 40. It additionally aids in compressing the collapsible sheath 50 by providing an added brace for the collar 55 as the collar pushes back collapsing the collapsible sheath 50.

In an alternative embodiment a stiffening wire 60, preferably stainless steel but optionally nitinol may also be incorporated longitudinally along the axis of the catheter 5 for extra stability and control.

In a fixed wire embodiment the guide wire lumen 15 may be replaced with just a guide wire, wherein the distal portion of the guide wire 20 is bonded to the distal tip 25.

The proximal portion of the catheter 5, as shown in FIGS. 1–3, comprises of a manifold system, generally designated 100, which includes a sliding member 110 slidably integrated between the distal and proximal end of the manifold. By retracting the sliding member 110 of the manifold 100, distal to proximal, the distal sheath 40 is retracted exposing the stent 35. The manifold 100 may further comprise a hydrating luer 130, which is preferably located on the distal end of the manifold 100 and is used to purge air from the catheter.

To prepare the stent delivery catheter 5 the stent 35 is compressed and loaded into the stent receiving portion 30 and covered by protective distal sheath 40. The distal sheath 40 remains covering the underlying stent 35 during the placement of the stent 35 by the delivery catheter 5 through the patient's vasculature. During the placement of the stent 35, protective distal sheath 40 protects the patient's vasculature from the stent 35.

FIGS. 1–3 illustrate three stages of the deployment of a self-expanding stent 35 using the preferred embodiment of the catheter of the present invention. FIG. 1 represents a loaded deployment catheter 5, with the stent 35 covered by the distal sheath 40 and the collapsible sheath 50 in its extended state. FIG. 2 shows the stent 35 partially deployed, with the distal sheath 40 retracted to cause the collapsible sheath to partially collapse. In the preferred embodiment the pull wire is attached to sliding member 110, which is used to retract sheath 40. As the sliding member 110 is pulled back the distal sheath 40 begins to retract. The stent is prevented from moving proximally with the sheath by the stopper and therefore, the stent 35 begins to release and expand while the collapsible sheath 50 begins to collapse upon itself in an accordion fashion. Since the distal sheath 40 does not slide back over the proximal sheath, but rather the collapsible sheath 50 collapses in place, the profile of the catheter 5 remains nearly the same. FIG. 3 shows the stent fully released. At this point the distal sheath 40 is fully retracted and the collapsible sheath 50 is compressed releasing the stent 35 to allow it to self-expand against the vessel wall 65. After the stent 35 is expanded and in place, the catheter 5 is withdrawn. It should be understood that a balloon expandable stent could also be utilized by arranging the stent around an optional placement balloon (not shown). Once the sheath 40 is fully retracted the placement balloon would be inflated through its inflation lumen (not shown) to deploy the stent.

Preferably the stent 35 is self expanding, such as a Nitinol™ stent, or it may be expanded by means of an internal balloon positioned under the stent 35 on the distal end of the inner core 40. Those skilled in the art will recognize other suitable materials and constructions which may be employed to serve substantially the same function.

The collapsible sheath is formed such that upon retraction of the distal sheath 40 the collapsible sheath 50 is compressed to a state approximately ⅕ of its longitudinally expanded state. The collapsible sheath 50 provides covering of the wire mechanism, eliminates the relative motion of the proximal edge of the distal sheath 40 and reduces the friction involved in retraction of the distal sheath 40. Unlike known retractable systems, the distal sheath does not retract over or under the proximal outer, which results in an increase in the profile of the catheter, an increase in friction as the distal sheath resists being pulled back over the proximal outer and a higher likelihood of hang ups due to the faulty engagement between the proximal end of the distal sheath and the guide catheter or vessel. In the present invention the collapsible sheath 50 compresses thereby providing space for the distal sheath 40 to retract without any encumbrances.

FIGS. 4 and 5 illustrate an alternative embodiment of the present invention. In this case the proximal outer 70 extends distally over the catheter, generally designated 90, up to a position in close proximity with the stopper 60 and the collapsible sheath 75 performs as the distal sheath. The distal end of the proximal outer 70 is adhered to the proximal end of the collapsible sheath 75 at point 80. In this embodiment the collar 55 is connected to collapsible sheath 75 at the distal end at point 85. As the pull back wire 45 is drawn proximally, the collapsible sheath 75 is retracted, collapsing upon itself, and begins to release. As discussed earlier, stopper 60 prevents the stent from moving proximally with the retracting sheath 75. FIG. 5 illustrates the fully retracted collapsible sheath 75 and the release of the stem 35 to its fully expanded position urging against the inner wall of the vessel 65.

FIG. 6 discloses an alternative embodimemt of the present invention. In this case the stent delivery system is generally designated 145 and the catheter 155 is comprised of a guide wire lumen 15 and a pull back lumen 150. The pull back lumen is axially connected to the guide wire lumen, travelling along the length of the guide wire lumen 15 up to the distal tip 25 at point 153, as the guide wire lumen continues through the distal tip 25. FIG. 7 illustrates the configuration of the catheter 155 from a cross-section perspective along lines 7—7 in FIG. 6. A stent 35 may be concentrically arranged around the catheter 15 near the distal end on the stent receiving portion 30. The device further comprises a retractable distal sheath 40 surrounding at least a portion of the stent 35. FIG. 6 shows the retractable distal sheath 40 partly retracted. The proximal end of the retractable distal sheath 40 is attached to the collapsible sheath 50 at point 143. The collapsible sheath 50 is concentrically arranged around the catheter 155 and is shown in FIG. 6 as partially collapsed. The proximal end of the collapsible sheath 50 is connected, preferably adhered, to a fixed anchoring device 140, preferably an annular collar, which is affixed to the catheter 155 at point 160. The fixed anchoring device 140 stabilizes the proximal end of the collapsible sheath 50 allowing it to collapse upon itself during retraction of the distal sheath 40. The pull back wire 45 travels, proximal to distal, through the pull back lumen 150 and exits through an axial slit (not shown) in the surface of the pull back lumen 150. The distal end of the pull back wire is attached to annular ring 55, which is in turn attached to the retractable distal sheath 40. During the application of the device the pull back wire 45 is retracted, sliding proximally through the axial slit in the pull back lumen, proximally retracting the distal sheath 40 causing the collapsible sheath 50 to collapse and freeing the stent 35 for delivery. The stopper 60 prevents the stent from moving proximally with the retracting sheath 75.

FIG. 8 illustrates a rapid exchange embodiment of the invention. The distal end of the catheter is structured and functions in the same fashion as that of the device shown in FIG. 1. The overall length of the catheter is approximately 135 cm, while the length of the guide wire lumen 15 is between approximately 5 cm to 35 cm from the distal tip 25 to a point where the guide wire lumen 15 and the guide wire 20 exit the catheter.

It should be understand that other mechanical methods of retracting the pull back wire, besides the manifold apparatus disclosed herein, may be employed.

It should also be understood that the retractable distal sheath 40 and the collapsible sheath 50 may comprise one continuous sheath, wherein the preform creases or pleats are incorporated only into the intended collapsible portion.

The design disclosed herein also aids in flushing the catheter. Since the catheter essentially is sealed to the distal tip 25 and has only one opening in the distal segment, that being the end portion of the guide wire lumen 15 at the distal tip 25, flushing is made easier and more efficient.

The present invention may be incorporated into both of the two basic types of catheters used in combination with a guide wire, commonly referred to as over-the-wire (OTW) catheters and rapid-exchange (RX) catheters. The construction and use of both over-the-wire and rapid-exchange catheters are well known in the art. The usable length of the delivery catheter is approximately 135 cm. For a rapid exchange catheter the distance from where the guide wire accesses the guide wire lumen to the distal tip will be approximately 5 cm to 35 cm.

The key features of the longitudinally collapsible sheath include, without limitation: low profile both proximally and distally when extended, relatively thin walls for low profile and large interior lumens, efficient packing upon collapse, flexible, pushable and trackable.

The above disclosure is intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent delivery system comprising:
    a catheter with a distal end and a proximal end;
    a stent concentrically arranged around the catheter near the distal end;
    a proximal outer sheath covering a portion of the catheter, wherein at least a portion of the distal end of the catheter is left exposed by the proximal outer sheath;
    a retractable distal sheath surrounding at least a portion of the stent;
    a pull back means having a distal end connected to the retractable distal sheath for retraction of the retractable distal sheath, and
    a collapsible sheath concentrically arranged around the catheter, attached to the proximal outer sheath and located between the retractable distal sheath and the proximal outer sheath;
    whereby when the pull back means is retracted proximally the distal sheath is retracted, causing the collapsible sheath to collapse and freeing the stent for delivery.

2. The stent delivery system as in claim 1, wherein the collapsible sheath has a distal end and a proximal end, the distal end being adhered to the retractable distal sheath and the proximal end being adhered to the proximal outer sheath.

3. The stent delivery system as in claim 2, wherein the stent is a self-expanding stent.

4. A stent deliver system as in claim 3, wherein the pull back means comprises a pull back wire.

5. The stent delivery system as in claim 4, wherein the pull back means further comprises an annular collar surrounding the catheter and longitudinally movable along the catheter, wherein the proximal end of the retractable distal sheath is connected to the annular collar and the distal end of the pull back wire are connected to the annular collar.

6. The stent delivery system as in claim 5, further comprising a stopper positioned on the catheter to prevent the stent from moving proximally as the distal sheath is retracted to expose the stent.

7. A stent delivery system as in claim 6, wherein the catheter comprises a guide wire lumen, the guide wire lumen being incompressible and flexible.

8. A stent delivery system as in claim 6, wherein the catheter comprises a guide wire, the guide wire being bonded to the distal end.

9. The stent delivery system as in claim 7, further comprising a pull back wire lumen which partially encloses the pull back wire and is at least partially covered by the proximal outer sheath.

10. The stent delivery system as in claim 8, further comprising a stiffening wire positioned longitudinally along the catheter.

11. The stent delivery system as in claim 7, wherein the guide wire lumen is a polymer encapsulated braid.

12. The stent delivery system as in claim 7, wherein the guide wire lumen is a polymer encapsulated coil.

13. The stent delivery system as in claim 11, further comprising a guide wire enclosed within the guide wire lumen.

14. The stent delivery system as in claim 13, comprising a plurality of pull back wires attached to the annular collar.

15. The stent delivery system as in claim 14, wherein the retractable distal sheath further includes a neck portion just proximal to the connection between the retractable distal sheath and the annular collar, which frictionally engages the annular collar and aids in retraction of the distal sheath.

16. The stent delivery system as in claim 14, wherein the proximal outer sheath comprises a high density polyethylene.

17. The stent delivery system as in claim 7, wherein the stent delivery system is an over-the wire catheter.

18. The stent delivery system as in claim 7, wherein the guide wire lumen is shorter than the catheter.

19. The stent delivery system of claim 18 wherein the catheter is 135 cm and the guide wire lumen is between 5 cm and 35 cm.

20. The stent delivery system as in claim 2, further comprising a balloon disposed under the stent, whereby after the retractable distal sheath is retracted the stent is expanded by inflating the balloon.

21. A stent delivery system comprising:
    a catheter with a distal end and a proximal end, the catheter having a stent receiving portion adapted to receive a stent near the distal end of the catheter and a distal tip arranged distal to the stent receiving portion;
    a stent concentrically arranged around the catheter within the stent receiving portion;
    a proximal outer sheath covering a portion of the catheter, wherein at least a portion of the distal end of the catheter is left exposed by the proximal outer sheath;
    a retractable distal sheath surrounding at least a portion of the stent and containing the stent in its reduced delivery configuration, the retractable distal sheath being collapsible; and
    a pull back means having a distal end connected to the retractable distal sheath, the pull back means being longitudinally movable; whereby when the pull back means is pulled proximally the distal sheath collapses upon itself in accordion fashion, freeing the stent for delivery.

22. The stent delivery system as in claim 21, wherein the retractable distal sheath comprises a proximal end, the proximal end being adhered to the proximal outer sheath.

23. The stent delivery system as in claim 22, wherein the stent is a self-expanding stent.

24. The stent delivery system as in claim 23, further comprising an annular collar, wherein the proximal end of the retractable distal sheath and the distal end of the pull back means are connected to the collar.

25. The stent delivery system as in claim 24, further comprising a stopper positioned to prevent the stent from moving proximally as the retractable distal sheath is retracted to expose the stent.

26. A stent deliver system as in claim 25, wherein the pull back means is a pull back wire.

27. A stent delivery system as in claim 26, wherein the catheter comprises a guide wire lumen, the guide wire being incompressible and flexible.

28. A stent delivery system as in claim 26, wherein the catheter comprises a guide wire, the guide wire being bonded to the distal tip.

29. The stem delivery system as in claim 27, further comprising a pull back wire lumen which partially encloses the pull back wire and is at least partially covered by the proximal outer sheath.

30. The stem delivery system as in claim 28, further comprising a stiffening wire positioned longitudinally along the catheter.

31. The stem delivery system as in claim 27, wherein the guide wire is a polymer encapsulated braid.

32. The stem delivery system as in claim 27, wherein the guide wire lumen is a polymer encapsulated coil.

33. The stem delivery system as in claim 31, further comprising a guide wire enclosed within the guide wire lumen.

34. The stent delivery system as in claim 33 comprising a plurality of pull back wires.

35. The stent delivery system as in claim 34, further comprising a neck portion situated in the retractable distal sheath just proximal to the attachment between the retractable distal sheath and the annular collar.

36. The stent delivery system as in claim 34, wherein the proximal outer sheath comprises a high density polyethylene.

37. The stent delivery system as in claim 27, wherein the stent delivery system is an over-the wire catheter.

38. The stent delivery system as in claim 27, wherein the catheter is 135 cm and the guide wire lumen is between 5 cm and 35 cm.

39. The stent delivery system as in claim 21, further comprising a balloon disposed under the stent within the stent receiving portion, whereby after the retractable distal sheath is retracted the stent is expanded by inflating the balloon.

40. A stent delivery system comprising:
a catheter with a distal end and a proximal end, the catheter including a guide wire lumen and a pull back lumen;
a stent concentrically arranged around the catheter near the distal end;
a retractable distal sheath surrounding at least a portion of the stent;
a pull back means, a portion of the pull back means housed in the pull back lumen, the pull back means having a distal end connected to the retractable distal sheath for retraction of the retractable distal sheath,
an anchoring device fixedly attached to the catheter, and
a collapsible sheath having proximal and distal ends and concentrically arranged around the catheter, the proximal end of the collapsible sheath being attached to the anchoring device and the distal end of the collapsible sheath being attached to the retractable distal sheath;
whereby when the pull back means is retracted proximally the distal sheath is retracted, causing the collapsible sheath to collapse and freeing the stent for delivery.

* * * * *

UNITED STATES PATENT AND TRADEMARK OFFICE
CERTIFICATE OF CORRECTION

PATENT NO. : 5,534,007
DATED : July 9, 1996
INVENTOR(S) : St. Germain et al

It is certified that error appears in the above-indentified patent and that said Letters Patent is hereby corrected as shown below:

On the face of the issued patent, please insert the following as additional "References Cited":

| | | | |
|---|---|---|---|
| 4,580,568 | 04/08/1986 | Gianturco | 128/345 |
| 4,848,343 | 07/18/1989 | Wallenstein et al | 128/345 |
| 4,998,539 | 03/12/1991 | Delsanti | 128/898 |
| 5,078,720 | 01/07/1992 | Burton et al | 606/108 |
| 5,026,377 | 06/25/1991 | Burton et al | 606/108 |
| 5,108,416 | 04/28/1992 | Ryan et al | 606/194 |
| 5,158,548 | 10/27/1992 | Lau et al | 604/96 |
| 5,180,368 | 01/19/1993 | Garrison | 604/104 |
| 5,192,297 | 03/09/1993 | Hull | 604/195 |
| 5,201,757 | 04/13/1993 | Heyn et al | 606/198 |
| 5,242,399 | 09/07/1993 | Lau et al | 604/104 |
| 5,306,294 | 04/26/1994 | Winston et al | 623/1 |
| 5,360,401 | 11/01/1994 | Turnland | 604/96 |
| 5,344,426 | 09/06/1994 | Lau et al | 606/198 |
| 5,372,600 | 12/13/1994 | Beyar et al | 604/96 |
| 0505686 A1 | 9/30/1992 | EP | |
| PCT/US91/03454 | 11/28/1991 | PCT | |

Signed and Sealed this

Seventeenth Day of December, 1996

Attest:

BRUCE LEHMAN

*Attesting Officer*   *Commissioner of Patents and Trademarks*